US012655416B2

(12) United States Patent
Zheng et al.

(10) Patent No.: US 12,655,416 B2
(45) Date of Patent: Jun. 16, 2026

(54) BIOLOGICAL SAMPLE SORTING METHOD, SURFACE ACOUSTIC WAVE MICROFLUIDIC CHIP, SYSTEM, TERMINAL, AND STORAGE MEDIUM

(71) Applicant: SHENZHEN INSTITUTES OF ADVANCED TECHNOLOGY, Shenzhen (CN)

(72) Inventors: Hairong Zheng, Shenzhen (CN); Long Meng, Shenzhen (CN); Weixing Chen, Shenzhen (CN); Lili Niu, Shenzhen (CN); Xiaoyu Cui, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 575 days.

(21) Appl. No.: 18/098,701

(22) Filed: Jan. 19, 2023

(65) Prior Publication Data

US 2023/0151313 A1 May 18, 2023

Related U.S. Application Data

(63) Continuation of application No. PCT/CN2020/106234, filed on Jul. 31, 2020.

(51) Int. Cl.
*C12N 13/00* (2006.01)
*C12M 1/42* (2006.01)
(Continued)

(52) U.S. Cl.
CPC ............... *C12N 13/00* (2013.01); *C12M 1/42* (2013.01); *G06N 3/045* (2023.01); *G06T 7/20* (2013.01)

(58) Field of Classification Search
CPC ......... C12N 13/00; C12M 1/42; C12M 23/16; C12M 41/36; C12M 47/04; G06N 3/045;
(Continued)

(56) References Cited

U.S. PATENT DOCUMENTS

2019/0302000 A1 10/2019 Lo et al.

FOREIGN PATENT DOCUMENTS

CN 104195028 A 12/2014
CN 107944360 A 4/2018
(Continued)

OTHER PUBLICATIONS

SSAW multichannel cell sorting, Ding et al 2012 (Year: 2012).*
(Continued)

*Primary Examiner* — Jianxun Yang

(57) ABSTRACT

A biological sample sorting method, a surface acoustic wave microfluidic chip, a system, a terminal, and a storage medium are disclosed. The method includes: injecting a mixed solution containing biological samples into a surface acoustic wave microfluidic chip, and applying a first sinusoidal signal thereto forming a standing wave sound field therein to aggregate the biological samples; collecting images of the aggregated biological samples; performing moving target identification and tracking on the images of the biological samples using a deep learning model, performing cluster analysis and classification on a tracked moving target to obtain a target sample, and generating a delay enabling signal of the target sample according to a moving speed of the target sample; and applying a second sinusoidal signal to the surface acoustic wave microfluidic chip according to the delay enable signal to move the target sample thus sorting out the target sample.

6 Claims, 5 Drawing Sheets

(51) Int. Cl.
  *G06N 3/045* (2023.01)
  *G06T 7/20* (2017.01)
(58) Field of Classification Search
  CPC ............. G06T 7/20; G06T 2207/20084; G06T
      7/0016; G06T 7/215; G06T 2207/10016;
        G06T 2207/10056; G06T 2207/30024;
                    G06T 7/254
  See application file for complete search history.

(56) References Cited

FOREIGN PATENT DOCUMENTS

| | | |
|---|---|---|
| CN | 109540771 A | 3/2019 |
| CN | 111274903 A | 6/2020 |

OTHER PUBLICATIONS

Image-Activated Cell Sorting, Nitta et al 2018 (Year: 2018).*
International Search Report issued in corresponding International application No. PCT/CN2020/106234, mailed Apr. 27, 2021.
Written Opinion of the International Searching Authority for No. PCT/CN2020/106234.

\* cited by examiner

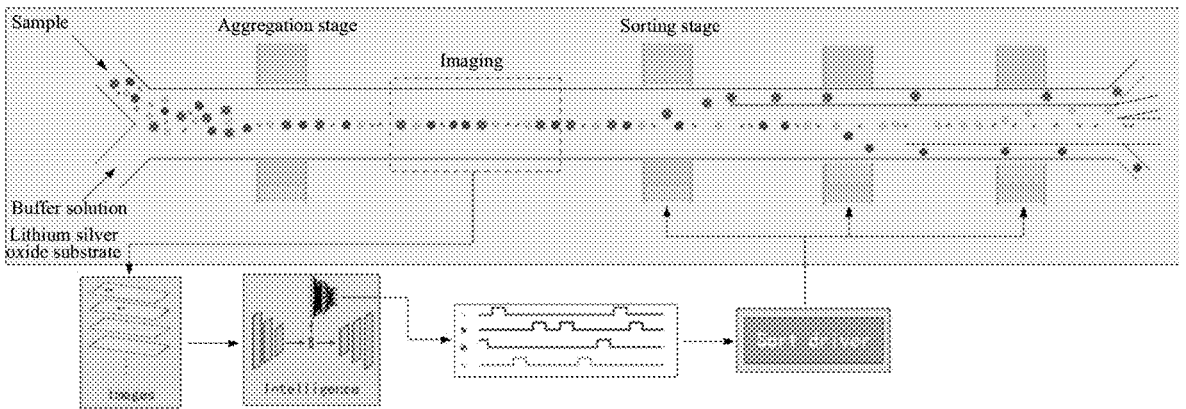
FIG. 4
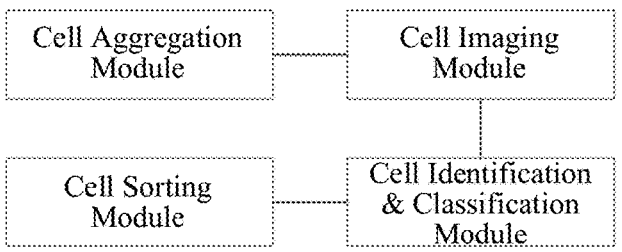
FIG. 5
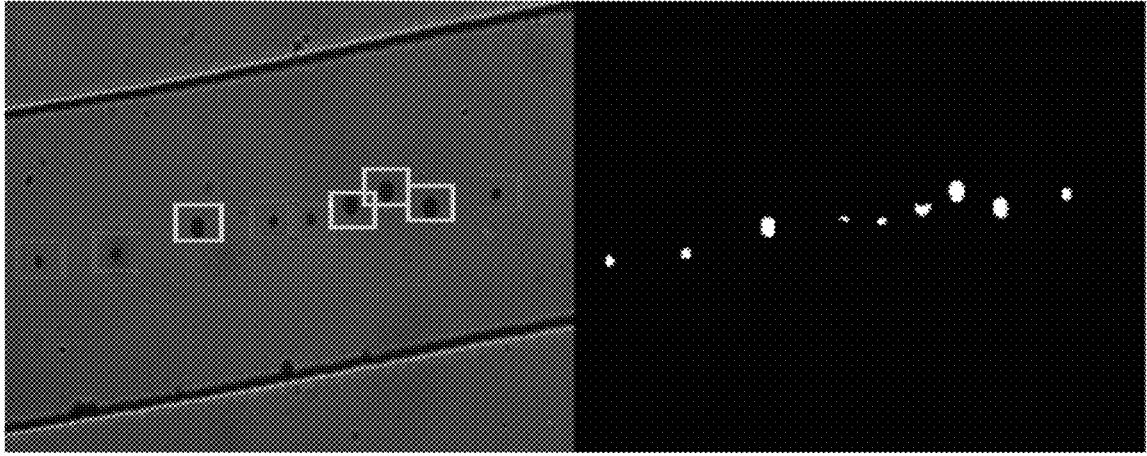
FIG. 6(a)                                       FIG. 6(b)

BIOLOGICAL SAMPLE SORTING METHOD, SURFACE ACOUSTIC WAVE MICROFLUIDIC CHIP, SYSTEM, TERMINAL, AND STORAGE MEDIUM

CROSS-REFERENCE TO RELATED APPLICATIONS

This application is a continuation of co-pending International Patent Application Number PCT/CN2020/106234, filed on Jul. 31, 2020, the disclosure of which is incorporated herein by reference in its entirety.

TECHNICAL FIELD

This application relates to the technical field of biological sample sorting, and more particularly relates to a biological sample sorting method, a surface acoustic wave microfluidic chip, a system, a terminal, and a storage medium.

BACKGROUND

A fundamental challenge in biology is studying the vast differences present between cells. Even those cells with the same genome differ in their composition, structure, and morphology because of their physiological functions. To understand and exploit these cell-to-cell differences, cells with specific morphological characteristics need to be sorted out from large heterogeneous populations.

Current specific cell sorting methods mainly include:

(1) Fluorescence-activated cell sorting (FACS). FACS can perform multi-parameter, rapid quantitative analysis and sorting of cells or biological particles that are moving in a fast linear flow state, and can accurately count and measure the fluorescence emitted by the combination of antibodies and antigens. With the advantages of rapidity and accuracy, FACS is used in the detection of tumor cells present in bone marrow and body fluids. Studies have found the sensitivity of flow cytometry to detect peripheral blood tumor cells is that one tumor cell can be detected in every 1000 peripheral blood lymphocytes. However, this technique has the following disadvantages: expensive equipment and lack of specific antigens, which also limit the promotion of this technique. When this technique is used to sort cells, the cell information is just a point on the scatter diagram, rather than the real cell image, and it can only process low-resolution data (about 20 light scattered and fluorescence signals) and be used for real-time data processing and manipulation (i.e., sorting), and it lacks of information on cell morphology, cell structure, and signal distribution at the subcellular level.

(2) Imaging flow cytometry (IFC). IFC combines the statistical power and fluorescence sensitivity of a standard flow cytometer with the spatial resolution and quantitative morphology of digital microscopy. This technique offers a convenient method to image and analyze cells directly in the blood, making it ideal for clinical applications. One disadvantage of this technique is that the evaluation of cell samples by imaging flow cytometry is complicated by many factors, and due to the limited speed of data transmission and image processing, high-dimensional data cannot be obtained, so real-time driving cannot be performed. A possible strategy to increase data processing throughput is to use multiple computers to process data in parallel, but this is usually limited to "offline" operations, thus requiring long turnaround times (more than a few seconds) and not allowing real-time startup.

(3) Intelligent fluorescence-activated cell sorting (IACS). Through flow cytometry, information is gathered from the interaction between light (usually a laser) and a flowing cell suspension, thereby measuring the forward and side scattered signals to derive the size, shape and fluorescent properties of the cells (elastic scattering), or the emission wavelength of a biomarker used as a fluorescent marker to specifically label cells (inelastic scattering), and identifying and collecting the target cell population. This technique uses a frequency division multiplexing microscope (FDM) to scan cells by converting a continuous wave laser beam into multiple laser beams with different modulation frequencies, and processes and merges the transmitted beams to obtain clear bright field and fluorescence images at the same time. However, this optical path system is extremely strict on time regulation, and the cost is extremely high. In addition, because of the use of fluorescent labeling reagents, the labeling reagents may inadvertently activate or inhibit bound cells prior to collection or during targeting, altering their behavior and leading to inaccurate cell analysis. Furthermore, the learning algorithm used is supervised learning, which requires a large amount of labeled data as a training set, which is costly and makes difficult to promote.

(4) Flow cytometry without fluorescent labeling. A novel flow cytometer can analyze cells by using their biophysical characteristics without fluorescent labeling, relying only on forward and side scattered signals. In time-stretch imaging, target cells are illuminated with spatially dispersed broadband pulses, encoding the spatial features of the target into the pulse spectrum within short sub-nanosecond pulse durations. Simultaneously, phase and intensity quantitative images are captured, providing rich features including protein concentration, optical loss, and cell morphology. The disadvantage of this technique is that it only relies on forward and side scattered signals as analysis sources in the absence of fluorescent label information, lacking sensitivity and selectivity, and the learning algorithm used is still supervised learning.

To sum up, the related specific cell sorting methods have certain limitations, such as the inability to ensure the sorting efficiency and cell viability as well as the system cost simultaneously, or it lacks of spatial information, thus resulting in weak specificity. Therefore, there is a need to develop an efficient, accurate, and non-damaging cell sorting method to solve the deficiencies present in the related art.

Imaging is essential for cell analysis because images can effectively convey certain information about cells, such as the shape and morphology of cells and the distribution or location of labeled biomolecules within cells. In recent years, due to high-speed imaging technology capable of acquiring information-rich images at high frame rates, a large number of cell images can be obtained in a short period of time, enabling the application of sophisticated tools, e.g., machine learning or deep learning, to image-based analysis. With the development of semiconductor technology, machine learning and deep learning shine in the field of image processing, greatly reducing the time consumption of the algorithm. However, even the related cell screening technology based on image analysis still needs fluorescent markers or manually labeled data as the basis for classification.

SUMMARY

This application provides a biological sample sorting method, a surface acoustic wave microfluidic chip, a system, a terminal, and a storage medium, aiming to solve the technical problem that the related specific cell sorting methods are based on supervised learning and require fluorescent markers as classification basis or annotation data thus resulting in limitations, and cannot ensure the sorting efficiency and cell activity as well as system cost simultaneously, or lack of spatial information, thereby leading to weak specificity.

In order to solve the above problems, this application provides the following technical solutions.

There is provided a biological sample sorting method, including the following steps:

injecting a mixed solution containing a biological samples into a surface acoustic wave microfluidic chip, and applying a first sinusoidal signal to the surface acoustic wave microfluidic chip thus forming a standing wave sound field in the surface acoustic wave microfluidic chip, making the biological samples gather at a node position in the standing wave sound field under the action of an acoustic radiation force;

collecting images of the aggregated biological samples;

performing moving target identification and tracking on the images of the biological samples using a deep learning model, performing cluster analysis and classification on a tracked moving target to obtain a target sample, and generating a delay enabling signal of the target sample according to a moving speed of the target sample;

applying a second sinusoidal signal to the surface acoustic wave microfluidic chip according to the delay enabling signal to control the movement of the target sample, so as to sort the target sample.

The technical solutions adopted in the embodiments of the present application further include: the surface acoustic wave microfluidic chip includes at least two pairs of interdigital transducers and a channel;

the at least two pairs of interdigital transducers are respectively located on both sides of an outer wall of the channel, and each pair of interdigital transducers respectively includes a first region for gathering biological samples, a third region for sorting target samples, and a transition region connecting the first region with said third region;

the channel includes two inlets and the same number of outlets as the target sample types, and the length of the channel is a quarter wavelength.

The technical solutions adopted in the embodiments of the present application further include the following. The operations of injecting a mixed solution containing biological samples into a surface acoustic wave microfluidic chip, and applying a first sinusoidal signal to the surface acoustic wave microfluidic chip thus forming a standing wave sound field in the surface acoustic wave microfluidic chip, making the biological samples gather at a node position in the standing wave sound field under the action of an acoustic radiation force include:

separately injecting a suspension containing the biological samples and a buffer solution into the channel through the two inlets, and applying a high-frequency continuous first sinusoidal signal to the first region of the at least two pairs of interdigital transducers through a signal generator thus forming a standing wave sound field in the channel, so that the biological samples scattered in the channel move to the node position of the standing wave sound field under the action of the sound radiation force and are arranged in a straight line.

The technical solutions adopted by the embodiments of the present application further include the following. The deep learning model includes an FCN network and a Siamese neural network, and the operations of performing moving target identification and tracking on the images of the biological samples using the deep learning model include:

performing moving target recognition on the biological samples in the images of the biological samples by using a moving target detection algorithm through the FCN model;

tracking the identified moving target by using a moving target tracking algorithm through the Siamese neural network and calculating the moving speed of the moving target in real time.

The technical solutions adopted in the embodiments of the present application further include the following. The Siamese neural network includes two convolutional neural networks that share weights. The inputs of the two convolutional neural networks are the current frame image and the sub-image containing the moving target in the previous frame, respectively. After sampling and encoding by the convolutional neural network, the result of the current frame image is convolved with the result of the sub-image containing the moving target, and the most similar area in the current frame to the previous frame is obtained to realize the tracking of the moving target.

The technical solutions adopted in the embodiments of the present application further include the following. The operations of performing cluster analysis and classification on a tracked moving target to obtain a target sample, and generating a delay enabling signal of the target sample according to a moving speed of the target sample include:

based on the online learning method, performing unsupervised analysis and classification on the tracked moving target according to the preset number of cell classification categories to obtain the target samples, and calculating the respective times for various target samples to reach the third region of the IDT according to the moving speeds, and generating respective delay enabling signals corresponding to various target samples according to the times.

The technical solutions adopted in the embodiments of the present application further include the following. The operation of applying a second sinusoidal signal to the surface acoustic wave microfluidic chip according to the delay enabling signal to control the movement of the target sample, so as to sort the target sample includes:

When the target sample reaches the third region of the IDT, driving the signal generator to apply a continuous second sinusoidal signal to the third region of the IDT through the respective delay enable signal thus forming at least one node of the standing wave sound field in the channel, and adjusting the voltage of the applied second sinusoidal signal to control the target sample to move to the node position of the standing wave sound field so as to sort the target sample.

Another technical solution adopted in the embodiments of the present application is a surface acoustic wave microfluidic chip for sorting biological samples, the surface acoustic wave microfluidic chip including at least two pairs of interdigital transducers and a channel.

The at least two pairs of interdigital transducers are respectively located on both sides of an outer wall of the channel, and each pair of interdigital transducers respectively includes a first region for gathering biological samples, a third region for sorting target samples, and a transition region connecting the first region with said third region.

The channel includes two inlets and the same number of outlets as the target sample types, and the length of the channel is a quarter wavelength.

Yet another technical solution adopted in the embodiments of the present application is a biological sample sorting system, including:

a sample aggregation module used to inject a mixed solution containing a biological samples into a surface acoustic wave microfluidic chip, and apply a first sinusoidal signal to the surface acoustic wave microfluidic chip thus forming a standing wave sound field in the surface acoustic wave microfluidic chip, making the biological samples gather at a node position in the standing wave sound field under the action of an acoustic radiation force;

a sample imaging module used to collect images of the aggregated biological samples;

a sample identification and classification module used to perform moving target identification and tracking on the images of the biological samples using a deep learning model, performing cluster analysis and classification on a tracked moving target to obtain a target sample, and generating a delay enabling signal of the target sample according to a moving speed of the target sample;

a sample sorting module used to apply a second sinusoidal signal to the surface acoustic wave microfluidic chip according to the delay enabling signal to control the movement of the target sample, so as to sort the target sample.

Still another technical solution adopted by the embodiments of the present application is a terminal, including a processor and a memory coupled to the processor, where the memory stores program instructions for performing the above biological sample sorting methods;

the processor is used for executing the program instructions stored in the memory to control biological sample sorting.

Still another technical solution adopted in the embodiments of the present application is a storage medium storing program instructions executable by a processor, and the program instructions are used to execute the biological sample sorting methods.

Compared with the related art, the beneficial effects produced by the embodiments of the present application are as follows. The biological sample sorting method, surface acoustic wave microfluidic chip, system, terminal, and storage medium according to the embodiments of the present application use the surface acoustic wave microfluidic chip as the experimental platform. In particular, under the action of sound waves, the biological samples are aggreagated, and with the help of deep learning, the image tracking algorithm based on unsupervised learning that does not need to label the training set data is used in combination with the clustering analysis algorithm to identify, track and analyze the target samples of images of the biological samples, and further a specific enabling signal is generated, which, while saving cost, can screen specific samples more efficiently, accurately, stably, and with high throughput without affecting the biological activity of the samples and with lower equipment cost, thereby enabling high flexibility, high scalability, and real-time automation for intelligent image processing and decision-making.

BRIEF DESCRIPTION OF DRAWINGS

FIG. 4 is an example diagram of an acoustic cell sorting process according to an embodiment of the present application.

FIG. 5 is a schematic diagram of a biological sample sorting system according to an embodiment of the present application.

FIGS. 6(a) and 6(b) are schematic diagrams illustrating the effect of tracking and classifying particles with different particle sizes according to an embodiment of the present application, wherein FIG. 6(a) shows the classification effect, a small ball is marked with a black box, and a large ball is marked with a white box; FIG. 6(b) illustrates identifying a moving target and generating a mask to determine the moving region.

DETAILED DESCRIPTION OF EMBODIMENTS

For a better understanding of the objectives, technical solutions, and advantages of the present application, hereinafter the present application will be described in further detail in connection with the accompanying drawings and some illustrative embodiments. It is to be understood that the specific embodiments described here are intended for the mere purposes of illustrating this application, instead of limiting.

In view of the deficiencies in the related art, the biological sample sorting method according to the embodiments of the present application constructs a surface acoustic wave microfluidic chip, and injects a suspension containing biological samples into the surface acoustic wave microfluidic chip for sample aggregation. After the sample image is collected through microscopic imaging, the deep learning model uses an unsupervised learning image tracking algorithm that does not need to label training set data in combination with a clustering analysis algorithm to identify, track and analyze the target sample on the sample image. Then, an enable signal is output depending on the flow velocity of the target sample, and the signal generator is driven by the enable signal to apply a continuous sinusoidal signal to the interdigital transducer to control the target sample to move to the node position of the standing wave sound field, thus finally sorting out the target sample.

This application can be applied to the sorting of biological samples such as acoustic cells, nano-biological particles, and tiny animals (such as nematodes). For ease of illustration, the following embodiments only use acoustic cell sorting as an example for detailed description.

Figure 1:
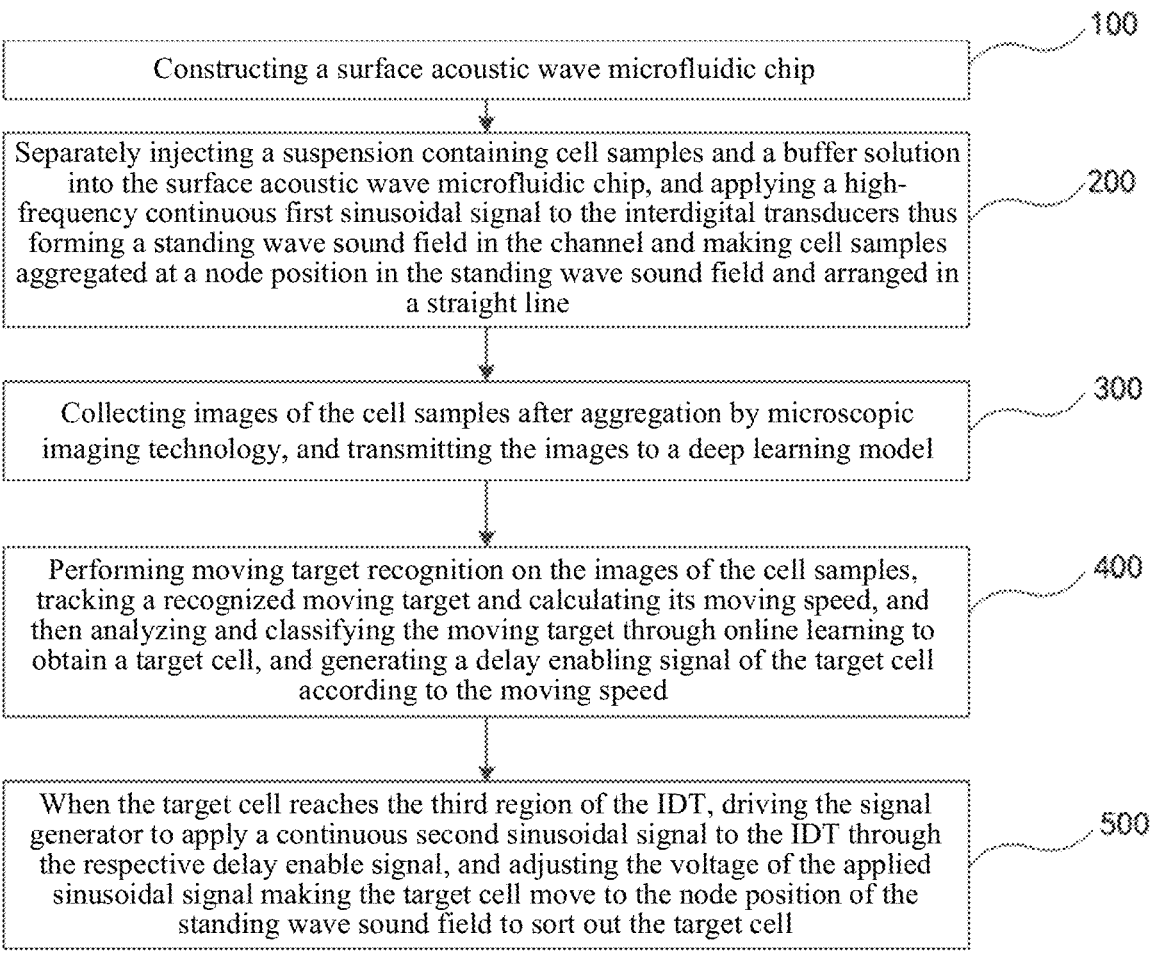
FIG. 1 is a flowchart of a biological sample sorting method according to an embodiment of the present application.

In particular, refer to FIG. 1, which is a flowchart of a biological sample sorting method according to an embodiment of the present application, where the biological sample is an acoustic cell. The biological sample sorting method of the embodiment of the present application includes the following steps:

Step 100: Constructing a surface acoustic wave microfluidic chip;

In step 100, the construction method of the surface acoustic wave microfluidic chip is as follows: using MEMS (Micro-Electro-Mechanical System) technology to prepare at least two pairs of interdigital transducers, and using a soft lithography process to manufacture a channel, and then binding the at least two pairs of interdigital transducers to the channel by plasma treatment, so that at least two pairs of interdigital transducers are located on both sides of the outer wall of the channel to form the surface acoustic wave microfluidic chip. Each interdigital transducer includes three parts:

A first region for gathering cell samples; the surface acoustic wave resonant frequency corresponding to the interdigitated electrodes in the first region is 15 MHz, and the corresponding finger width is 65 microns;

A third region for sorting target cells; the surface acoustic wave resonant frequency corresponding to the interdigitated electrodes in the third region is 30 MHz, and the corresponding finger width is 32.5 microns;

A transition region used to connect the first area to the third area; because the finger widths of the first region and the third region are different, a transition region is required for connection, and because the transition region has a large slope and insertion loss, cell sorting cannot be performed.

In the embodiments of the present application, in order to obtain a relatively large electromechanical coupling coefficient, the piezoelectric substrate of the interdigital transducer is a 128° YX double-sided polished lithium niobate crystal. In practical applications, multiple pairs of interdigital transducers can be prepared depending on the number of types of cells to be sorted to increase throughput, and at the same time, the efficiency and accuracy of cell sorting can be improved based on cascade sorting.

In the embodiments of the present application, the width of the channel is 65 microns, and the depth is 50 microns, which can be set depending on actual applications. The channel includes two inlets, which are respectively used to inject suspension containing cell samples and buffer solution, and the outlet of the channel can be set according to the number of types of cells to be sorted. The channel includes a PDMS (polydimethylsiloxane) channel or a channel made of other polymer materials and single crystal silicon, and in this embodiment of the present application the channel may be a PDMS channel.

Based on the above, the embodiments of the present application adopt the mature MEMS technology to prepare the surface acoustic wave microfluidic chip, which can maintain good consistency of performance, and is low in cost and convenient for mass production.

Step 200: separately injecting the suspension containing the cell samples and the buffer solution into the channel of the surface acoustic wave microfluidic chip through a syringe pump, and applying a high-frequency continuous first sinusoidal signal to the interdigital transducer through the signal generator thus forming a standing wave sound field in the channel, so that the cell samples are gathered at the node position in the standing wave sound field (that is, the center of the channel) and arranged in a straight line;

In step 200, after the suspension containing the cell samples and the buffer solution are separately injected into the channel, the cell samples are evenly scattered in the channel. After applying the continuous first sinusoidal signal to the interdigital transducer at the same time, a planar standing wave sound field is constructed in the channel, and the acoustic radiation force experienced by the cell samples in the standing wave acoustic field can be expressed as:

$$F_r = -\left(\frac{\pi p_0^2 V_c \beta_w}{2\lambda}\right) \cdot \phi(\beta, \rho) \cdot \sin(2kx) \qquad (1)$$

-continued $$\phi(\beta, \rho) = \frac{5\rho_c - 2\rho_w}{2\rho_c + \rho_w} - \frac{\beta_c}{\beta_w} \qquad (2)$$

Figure 2:
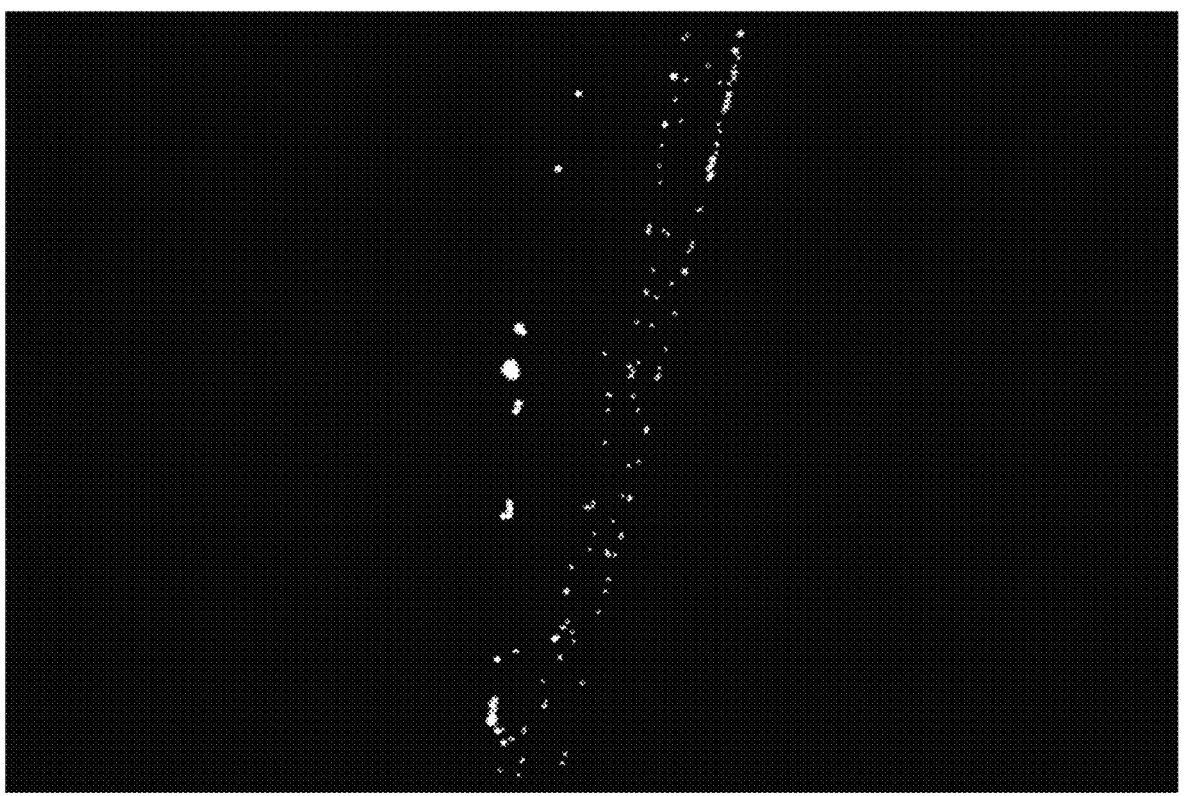
FIG. 2 shows the stress of fluorescent beads with different particle sizes in the standing wave sound field.

From formula (1), it can be concluded that the acoustic radiation force ($F_r$) is proportional to the particle volume ($V_c$), the frequency of the applied sinusoidal signal ($1/\lambda$) and the acoustic contrast factor ($\Phi(\beta, \rho)$). From formula (2) it can be known that the acoustic contrast coefficient ($\Phi(\beta, \rho)$) depends on the particle density ($\rho_c$), the density of the suspension medium ($\rho_w$), the compressibility ratio of the particles ($\beta_c$), and the compressibility ratio of the medium ($\beta_w$). Since the particle volume is proportional to the cubic radius of the particle, the acoustic radiation force is strongly dependent on the particle size. Except for a few cases where the density component is equal to the compressible component in formula (2), the particle will be subjected to the acoustic radiation force shown in formula (1), and the sign of the acoustic contrast coefficient will determine the direction of particle motion. In particular, FIG. 2 shows the stress situation of fluorescent beads with different particle sizes in the standing wave sound field. It can be found that all particles move towards the node position of the standing wave sound field, and the particles with larger particle sizes move at a higher speeds, which indicates that the particle size is proportional to the acoustic radiation force when the density is similar, and the particles with larger particle sizes are more susceptible to the action of sound waves.

In the embodiments of this application, since the density of the cells is greater than that of the liquid medium, the cells will move to the nodes in the standing wave sound field. The length of the channel is a quarter of a wavelength, so that the cells are gathered at the node position in the standing wave sound field, and the cells would be arranged in a straight line, which is convenient for subsequent cell identification and tracking, and reduces unnecessary time overhead.

In the embodiments of this application, the cell aggregation method used is acoustic tweezers, which does not generate acceleration due to hydrodynamic aggregation, thereby achieving a higher particle analysis rate. In addition, this application does not require the use of sheath flow, which can minimize fluid consumption and harmful waste output, thus protecting the biological effects of cells to a greater extent.

Figure 3:
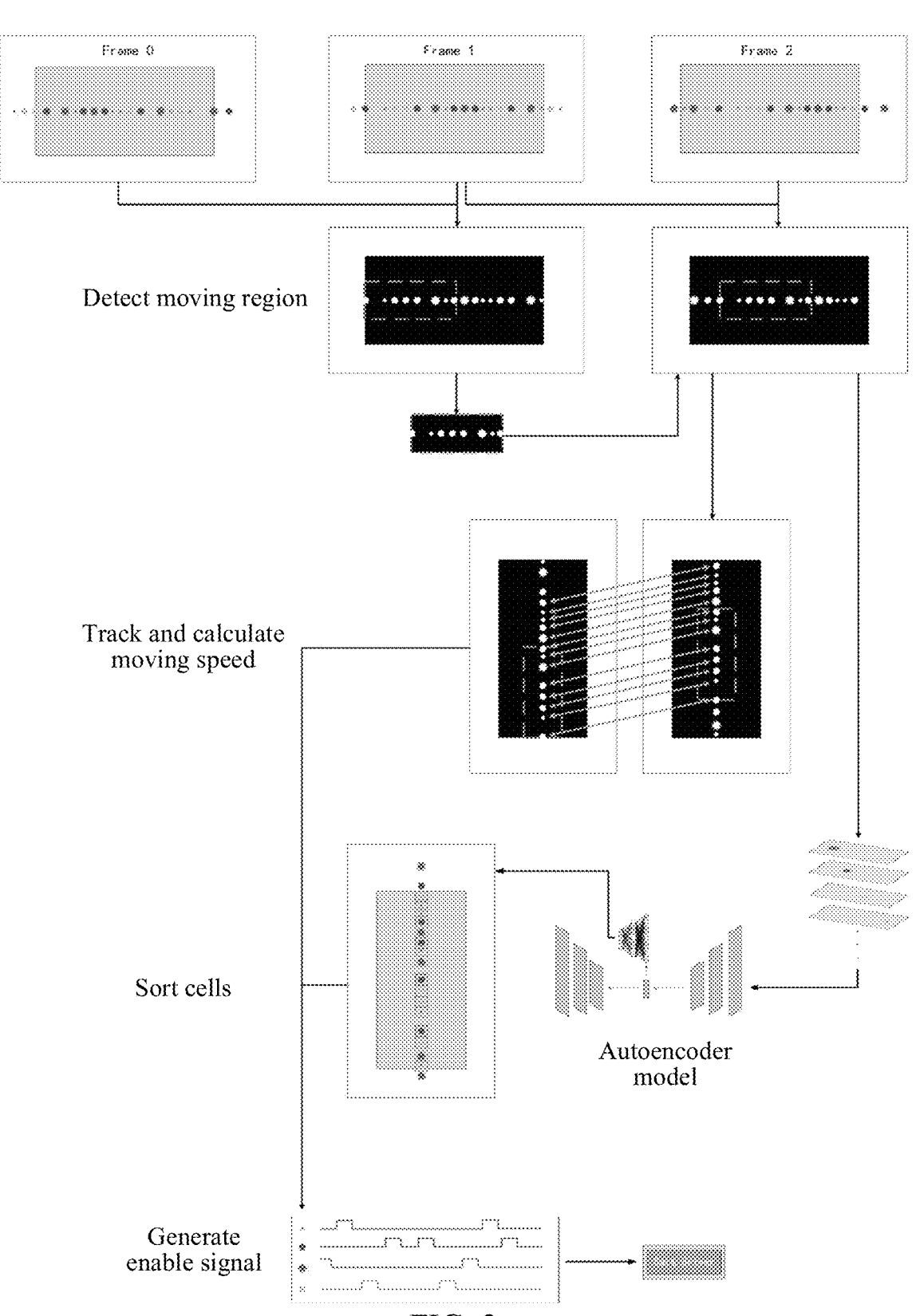
FIG. 3 is a schematic diagram of an image analysis and classification process of a deep learning model according to an embodiment of the present application.

Step 300: collecting the cell sample image after aggregation by microscopic imaging technology, and transmitting the image to the deep learning model;

Step 400: identifying by the deep learning model the moving target on the cell sample image, tracking the identified moving target and calculating its moving speed, and then analyzing and classifying the moving target through online learning to obtain target cells, and generating delay enabling signals for various target cells depending the moving speeds;

In step 400, as shown in FIG. 3, where there is illustrated a schematic diagram of the image analysis and classification process of the deep learning model according to the embodiments of the present application. The deep learning model includes FCN (Fully Convolutional Networks) network and Siamese network based on the frame difference method. The recognition, tracking and classification of cells by the deep learning model include the following steps:

Step 401: Using the FCN model to identify the moving target of the unmarked cell sample in the cell sample image by using the moving target detection algorithm, and removing irrelevant pixels;

In some embodiments, the FCN model uses the frame difference method to perform moving target recognition on the cell sample image. When there is a moving target in the image, the pixel values of adjacent frames will be different, that is, after differentiation of two frames, the value of a static region is 0, and the region with a moving target has a non-zero value due to grayscale changes. When the numerical difference of the same region in two adjacent frames exceeds the set threshold, it can be judged that the region is a moving region, so as to realize the recognition of moving targets. It can be understood that in other embodiments of the present application, other moving target detection algorithms may also be used, such as optical flow method or other moving target detection algorithms that identify moving regions in future frames based on information differences between previous and subsequent frames.

Step 402: Tracking the identified moving target through a Siamese neural network and calculating its moving speed in real time;

A Siamese neural network includes two convolutional neural networks that share weights. The inputs of the two convolutional neural networks are the current frame image and the sub-image containing the moving target in the previous frame, respectively. After sampling and encoding by the network, the result of the current frame image is convolved with the result of the sub-image containing the moving target, and the most similar area in the current frame to the previous frame is obtained to realize the tracking of the moving target.

In the embodiments of the present application, the moving target tracking algorithm may be implemented through template matching, or through a correlation filter.

Step 403: Based on the online learning method, performing unsupervised analysis and classification on the tracked moving target according to the number of cell classification categories set in advance to obtain the target cells, and calculating the respective times for various target cells to reach the third region of the IDT according to the moving speeds, and generating respective delay enabling signals corresponding to various target cells according to the times;

This embodiment of the present application conducts unsupervised analysis and classification on the tracked moving targets through online learning, without annotation data and prior training of large data sets, which saves a lot of data annotation costs. In the process of use, real-time learning is performed on each piece of data encountered, cluster analysis is performed according to the set number of classifications to search for unknown cell subspecies. At the same time, since this application adopts online learning method, the accuracy will continue to improve during continuous use. In addition, integrated learning can be performed based on the last model to obtain accurate classification results. Furthermore, the versatility of online learning provide guarantee for large-scale use.

It can be understood that in other embodiments of the present application, other image analysis algorithms such as reinforcement learning methods can also be used to analyze moving targets. Weakly supervised learning can also be performed through a small amount of annotation data, or data analysis can be performed through self-encoding before classification.

Step 500: When the target cell reaches the third region of the IDT, driving the signal generator to apply a continuous second sinusoidal signal to the IDT through the respective delay enable signal, and adjusting the voltage of the applied sinusoidal signal, so that the target cell moves to the node position of the standing wave sound field to realize the sorting of the target cell;

In step 500, in microfluidics, the Reynolds number of the fluid is very low, and the fluid is laminar. The laminar flow effect makes the aggregated cell samples move along the center of the lumen after passing through the first region and the transition region of the interdigital transducer. The delay enabling signal drives the interdigital transducer to form a standing wave sound field in the channel. After receiving the delay enable signal, a certain continuous second sinusoidal signal is applied to the interdigital transducer through the signal generator, and two nodes of the standing wave sound field are formed in the channel, which are respectively located on both sides of the channel adjacent to the inner wall. According to formulas (1) and (2), the acoustic radiation force depends largely on the particle size, and when the particle size is similar, the target cells that need to be sorted can be obtained based on image analysis. According to the moving speed of the target cell, the time to reach the third region of the interdigital transducer is pre-calculated. When the target cell reaches the region, a continuous second sinusoidal signal is immediately applied through the signal generator, and the movement of the target cell is controlled by adjusting its applied voltage, so that the target cell moves to the two node positions of the standing wave sound field. Non-target cells do not activate the signal that generates the acoustic field, and therefore are not affected by the force of the acoustic radiation, but still move along the center of the lumen under the drag force caused by the laminar flow. In particular, as shown in FIG. 4, there is illustrated an example diagram of the cell sorting process according to the embodiments of the present application.

Furthermore, when sorting multiple (more than two) types of cells, multiple interdigital transducers can be cascaded as needed. Under the action of the acoustic radiation force, the first-stage target cells move to the node positions in the standing wave sound field to realize the sorting of the first-stage target cells. However, other cells are not able to resist the drag force caused by laminar flow under the small acoustic radiation force, and they still move along the center of the channel. When reaching the second-stage interdigital transducer, the first-stage operation is repeated to sort the second-stage target cells, thereby achieving the purpose of multi-stage sorting.

In the embodiments of the present application, Ethernet is used for data exchange between cell imaging, analysis, and drive. Ethernet uses Internet protocols to send and receive signals between multiple computers, multiple sensors, and multiple actuators, enabling high flexibility, high scalability, and real-time automated operations for intelligent image processing and decision-making.

In the embodiments of the present application, the purpose of cell sorting is achieved through image analysis, without the need for fluorescent markers, which reduces costs while avoiding the impact of specific antigens, and ensures the biological activity of cells. It can be understood that cell sorting can also be performed on the basis of fluorescent information of fluorescent markers combined with spatial information to increase the specificity of cell sorting. Alternatively, optical, electrical, magnetic and other methods may be used to achieve cell sorting on the basis of the image analysis results.

In the embodiments of the present application, the aggregation and sorting of cells only rely on the image analysis results to adjust the radio frequency signal of the interdigital transducer without changing the structure of the surface acoustic wave microfluidic chip, which reduces the cost of repeatedly manufacturing chips, and has favorable universal applicability.

Referring to FIG. 5, there is shown a schematic diagram of a biological sample sorting system according to an embodiment of the present application. The biological sample sorting system according to the embodiments of the present application includes:

a cell aggregation module used to separately inject the suspension containing the cell samples and the buffer solution into the surface acoustic wave microfluidic chip, and apply a high-frequency continuous sinusoidal signal to the interdigital transducer through the signal generator thus forming a standing wave sound field in the channel, so that the cell samples are gathered at the node position in the standing wave sound field (that is, the center of the channel) and arranged in a straight line;

The construction method of the surface acoustic wave microfluidic chip is as follows: using MEMS technology to prepare at least two pairs of interdigital transducers, and using a soft lithography process to manufacture a channel, and then binding the at least two pairs of interdigital transducers to the channel by plasma treatment, so that at least two pairs of interdigital transducers are located on both sides of the outer wall of the channel to form the surface acoustic wave microfluidic chip. Each interdigital transducer includes three parts:

A first region for gathering cell samples; the surface acoustic wave resonant frequency corresponding to the interdigitated electrodes in the first region is 15 MHz, and the corresponding finger width is 65 microns;

A third region for sorting target cells; the surface acoustic wave resonant frequency corresponding to the interdigitated electrodes in the third region is 30 MHz, and the corresponding finger width is 32.5 microns;

A transition region used to connect the first area to the third area; because the finger widths of the first region and the third region are different, a transition region is required for connection, and because the transition region has a large slope and insertion loss, cell sorting cannot be performed.

In the embodiments of the present application, in order to obtain a relatively large electromechanical coupling coefficient, the piezoelectric substrate of the interdigital transducer is a 128° YX double-sided polished lithium niobate crystal. In practical applications, multiple pairs of interdigital transducers can be prepared depending on the number of types of cells to be sorted to increase throughput, and at the same time, the efficiency and accuracy of cell sorting can be improved based on cascade sorting.

In the embodiments of the present application, the width of the channel is 65 microns, and the depth is 50 microns, which can be set depending on actual applications. The channel includes two inlets, which are respectively used to inject suspension containing cell samples and buffer solution, and the outlet of the channel can be set according to the number of types of cells to be sorted. The channel includes a PDMS channel or a channel made of other polymer materials and single crystal silicon, and in this embodiment of the present application the channel may be a PDMS channel.

Based on the surface acoustic wave microfluidic chip with the above structure, after the suspension containing the cell samples and the buffer solution are separately injected into the channel, the cell samples are evenly scattered in the channel. After applying the continuous first sinusoidal signal to the interdigital transducer at the same time, a planar standing wave sound field is constructed in the channel, and the acoustic radiation force experienced by the cell samples in the standing wave acoustic field can be expressed as:

$$F_r = -\left(\frac{\pi p_0^2 V_c \beta_w}{2\lambda}\right) \cdot \phi(\beta, \rho) \cdot \sin(2kx) \tag{1}$$

$$\phi(\beta, \rho) = \frac{5\rho_c - 2\rho_w}{2\rho_c + \rho_w} - \frac{\beta_c}{\beta_w} \tag{2}$$

From formula (1), it can be concluded that the acoustic radiation force ($F_r$) is proportional to the particle volume ($V_c$), the frequency of the applied sinusoidal signal ($1/\lambda$) and the acoustic contrast factor ($\Phi$). From formula (2) it can be known that the acoustic contrast coefficient ($\Phi$) depends on the particle density ($\rho_c$), the density of the suspension medium ($\rho_w$), the compressibility ratio of the particles ($\beta_c$), and the compressibility ratio of the medium ($\beta_w$). Since the particle volume is proportional to the cubic radius of the particle, the acoustic radiation force is strongly dependent on the particle size. Except for a few cases where the density component is equal to the compressible component in formula (2), the particle will be subjected to the acoustic radiation force shown in formula (1), and the sign of the acoustic contrast coefficient will determine the direction of particle motion. In particular, FIG. 2 shows the stress situation of fluorescent beads with different particle sizes in the standing wave sound field. It can be found that all particles move towards the node position of the standing wave sound field, and the particles with larger particle sizes move at a higher speeds, which indicates that the particle size is proportional to the acoustic radiation force when the density is similar, and the particles with larger particle sizes are more susceptible to the action of sound waves.

In the embodiments of this application, since the density of the cells is greater than that of the liquid medium, the cells will move to the nodes in the standing wave sound field. The length contained in the channel is a quarter of a wavelength, so that the cells are gathered at the node position in the standing wave sound field, and the cells would be arranged in a straight line, which is convenient for subsequent cell identification and tracking, and reduces unnecessary time overhead.

a cell imaging module used to collect the cell sample image after aggregation by microscopic imaging technology, and transmit the image to the deep learning model;

a cell recognition and classification module used to identify the moving target on the cell sample image using a deep learning model, track the identified moving target and calculating its moving speed, and then analyze and classify the moving target through online learning to obtain target cells, and generate delay enabling signals for various target cells depending the moving speeds; The deep learning model includes FCN network and Siamese network based on the frame difference method. The recognition, tracking and classification of cells by the deep learning model include the following:

Using the FCN model to identify the moving target of the unmarked cell sample in the cell sample image by using the moving target detection algorithm, and removing irrelevant pixels. In some embodiments, the FCN model uses the frame difference method to perform moving target recognition on the cell sample image. When there is a moving target in the image, the pixel values of adjacent frames will be different, that is, after differentiation of two frames, the value of a static region is 0, and the region with a moving target has a non-zero value due to grayscale changes. When the numerical difference of the same region in two adjacent frames exceeds the set threshold, it can be judged that the region is a moving region, so as to realize the recognition of moving targets. It can be understood that in other embodiments of the present application, other moving target detection algorithms may also be used, such as optical flow method or other moving target detection algorithms that identify moving regions in future frames based on information differences between previous and subsequent frames.

Further included is tracking the identified moving target through a Siamese neural network and calculating its moving speed in real time;

A Siamese neural network includes two convolutional neural networks that share weights. The inputs of the two convolutional neural networks are the current frame image and the sub-image containing the moving target in the previous frame, respectively. After sampling and encoding by the network, the result of the current frame image is convolved with the result of the sub-image containing the moving target, and the most similar area in the current frame to the previous frame is obtained to realize the tracking of the moving target.

Based on the online learning method, unsupervised analysis and classification are performed on the tracked moving target according to the number of cell classification types set in advance, and corresponding delay enabling signals are generated for various target cells depending on their moving speeds.

a cell sorting module used to: when the target cell reaches the third region of the IDT, drive the signal generator to apply a continuous second sinusoidal signal to the IDT through the respective delay enable signal, and adjust the voltage of the applied sinusoidal signal, so that the target cell moves to the node position of the standing wave sound field to realize the sorting of the target cell;

The laminar flow effect makes the aggregated cell samples move along the center of the lumen after passing through the first region and the transition region of the channel. The delay enabling signal drives the interdigital transducer to form a standing wave sound field in the channel. After receiving the delay enable signal, a certain continuous second sinusoidal signal is applied to the interdigital transducer through the signal generator, and two nodes of the standing wave sound field are formed in the channel, which are respectively located on both sides of the channel adjacent to the inner wall. According to formulas (1) and (2), the acoustic radiation force depends largely on the particle size, and when the particle size is similar, the target cells that need to be sorted can be obtained based on image analysis. According to the moving speed of the target cell, the time to reach the third region of the interdigital transducer is pre-calculated. When the target cell reaches the region, a continuous second sinusoidal signal is immediately applied through the signal generator, and the movement of the target cell is controlled by adjusting its applied voltage, so that the target cell moves to the two node positions of the standing wave sound field. Non-target cells do not activate the signal that generates the acoustic field, and therefore are not affected by the force of the acoustic radiation, but still move along the center of the lumen under the drag force caused by the laminar flow.

In order to verify the feasibility and effectiveness of the embodiments of this application, two kinds of particles with different particle sizes were mixed as the experimental sample, which is then injected into the PDMS channel at a speed of 10 μl/min for experiment. As shown in FIGS. 6(a) and 6(b), there is depicted a schematic diagram of the effect of tracking and classifying particles with different particle sizes, in which FIG. 6(a) shows the classification effect, where a small ball is marked with a black box, and a large ball is marked with a white box; FIG. 6(b) shows identifying moving targets and generating a mask to determine the moving region. The pressure of the syringe pump drives the sample suspension, and the particles move rapidly in the channel. When moving into the imaging range, according to the changes of the two subsequent frames, the moving (particle) region is identified and a mask is generated. According to each effective region of the mask, a particle sub-image is extracted from the original image, and after the classification algorithm, the types of particles in each sub-image as shown in FIG. 6(a) are identified. Experimental results show that the embodiments of the present application can identify and sort unknown new biological samples more intelligently, effectively, accurately and quickly.

Figure 7:
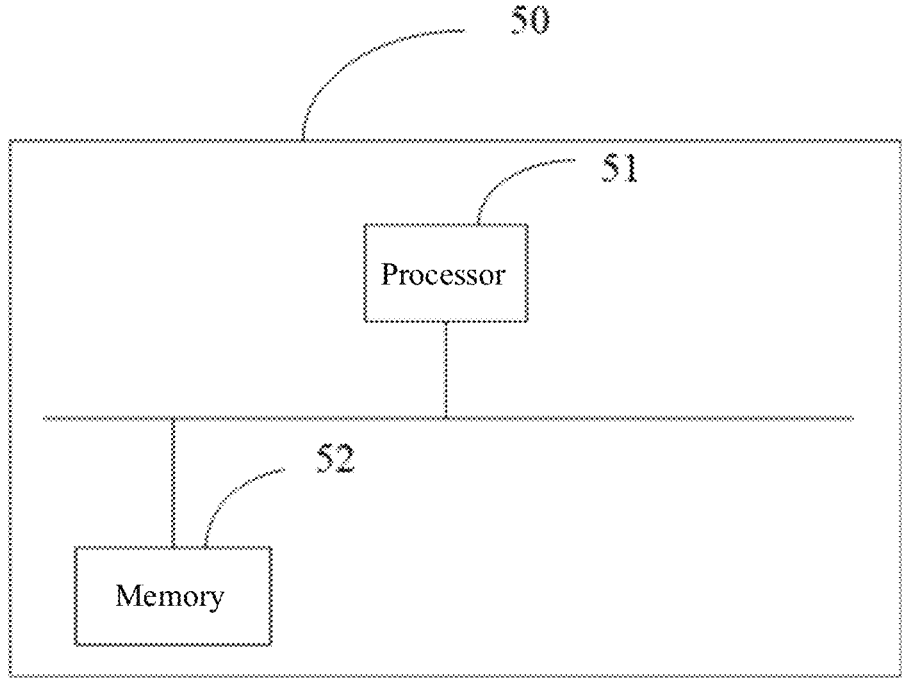
FIG. 7 is a schematic diagram of a terminal according to an embodiment of the present application.

Referring to FIG. 7, there is shown a block diagram of a terminal according to an embodiment of the present application. The terminal 50 includes a processor 51 and a memory 52 coupled to the processor 51.

The memory 52 stores program instructions for performing the above biological sample sorting methods.

The processor 51 is used for executing the program instructions stored in the memory 52 to control biological sample sorting.

The processor 51 may also be referred to as a CPU (Central Processing Unit). The processor 51 may include a GPU (Graphics Processing Unit) for image processing and analysis. The processor 51 may be an integrated circuit chip with signal processing capabilities. The processor 51 may also be a general-purpose processor, a digital signal processor (DSP), an application-specific integrated circuit (ASIC), an field-programmable gate array (FPGA) or other programmable logic devices, discrete gate or transistor logic devices, or discrete hardware components. A general purpose processor may be a microprocessor or any conventional processor or the like.

Figure 8:
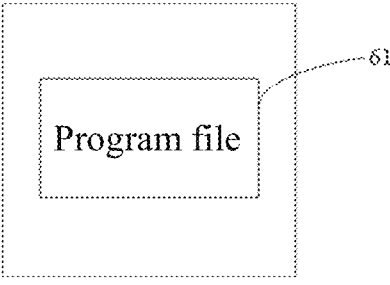
FIG. 8 is a schematic diagram of a storage medium according to an embodiment of the present application.

Referring to FIG. 8, there is shown a schematic diagram of a storage medium according to an embodiment of the present application. The storage medium in this embodiment of the present application stores the program files 61 capable of performing all the above-mentioned methods. The program files 61 may be stored in the above-mentioned storage medium in the form of a software product, including several instructions to enable a computer device (which can be a personal computer, server, or network device, etc.) or a processor (processor) to execute some or all of the steps of the methods illustrated in various embodiments of the present disclosure. The aforementioned storage media include: U disk, mobile hard drive, read-only memory (ROM), random access memory (RAM), magnetic disk, or optical disk or any other media that can store program codes, or computers, servers, mobile phones, terminal devices such as tablets.

The biological sample sorting method, surface acoustic wave microfluidic chip, system, terminal, and storage medium according the embodiments of the present application use the surface acoustic wave microfluidic chip as the experimental platform. In particular, under the action of sound waves, the biological samples are gathered into a straight line, and with the help of deep learning, the image tracking algorithm based on unsupervised learning that does not need to label the training set data is used in combination with the clustering analysis algorithm to identify, track and analyze the target samples of images of the biological samples, and further a specific enabling signal is generated and realize the sorting of biological samples by adjusting the amplitude and frequency of the sound wave. Compared with the related art, embodiments of the present application do not require annotation data and large-scale data set training, which, while saving cost, can screen specific samples more efficiently, accurately, stably, and with high throughput without affecting the biological activity of the samples and with lower equipment cost, thereby enabling high flexibility, high scalability, and real-time automation for intelligent image processing and decision-making.

The above description of the disclosed embodiments enables those having ordinary skill in the art to implement or use the present application. Various modifications to these embodiments will be evident to those having ordinary skill in the art, and the general principles defined in the present application may be implemented in other embodiments without departing from the spirit or scope of the present application. Therefore, the present application will not be limited to the embodiments disclosed herein, but should be interpreted to cover the widest scope consistent with the principles and novel features disclosed in the present application.

What is claimed is:

1. A biological sample sorting method, comprising:

injecting a mixed solution containing biological samples into a surface acoustic wave microfluidic chip, and applying a first sinusoidal signal to the surface acoustic wave microfluidic chip thus forming a standing wave sound field in the surface acoustic wave microfluidic chip and making the biological samples aggregate at a node position in the standing wave sound field under the action of an acoustic radiation force;

collecting images of the aggregated biological samples;

performing moving target identification and tracking on the images of the biological samples using a deep learning model, performing cluster analysis and classification on a tracked moving target to obtain at least one target sample, and generating a delay enabling signal of the at least one target sample according to a moving speed of the at least one target sample; and applying a second sinusoidal signal to the surface acoustic wave microfluidic chip according to the delay enabling signal to control the at least one target sample to move thus sorting out the at least one target sample;

wherein the deep learning model comprises a Fully Convolutional Network (FCN) network and a Siamese neural network, and wherein the operations of performing moving target identification and tracking on the images of the biological samples comprise:

performing moving target recognition on the biological samples in the images of the biological samples by using a moving target detection algorithm based on the FCN model; and tracking a recognized moving target by using a moving target tracking algorithm and calculating a moving speed of the moving target in real time based on the Siamese neural network.

2. The biological sample sorting method as recited in claim 1, wherein the surface acoustic wave microfluidic chip comprises at least two pairs of interdigital transducers and a channel;

wherein the at least two pairs of interdigital transducers are respectively disposed on two sides of an outer wall of the channel; each pair of interdigital transducers comprises a first region used for gathering the biological samples, a third region for sorting out the at least one target sample, and a transition region connecting the first region with the third region; and wherein the channel comprises two inlets and a same number of outlets as types of the at least one target sample, and wherein a length of the channel is a quarter wavelength.

3. The biological sample sorting method as recited in claim 2, wherein the operations of injecting a mixed solution containing biological samples into a surface acoustic wave microfluidic chip, and applying a first sinusoidal signal to the surface acoustic wave microfluidic chip thus forming a standing wave sound field in the surface acoustic wave microfluidic chip and making the biological samples aggregate at a node position in the standing wave sound field under the action of an acoustic radiation force comprise:

separately injecting a suspension containing the biological samples and a buffer solution into the channel through the two inlets, and applying a high-frequency continuous first sinusoidal signal to the first region of the at least two pairs of interdigital transducers through a signal generator thus forming the standing wave sound field in the channel and making the biological samples scattered in the channel move to the node position of the standing wave sound field under the action of the sound radiation force and be arranged in a straight line.

4. The biological sample sorting method as recited in claim 2, wherein the operations of performing cluster analysis and classification on a tracked moving target to obtain a target sample, and generating a delay enabling signal of the target sample according to a moving speed of the target sample comprise:

based on an online learning method, performing unsupervised analysis and classification on the tracked moving target according to a preset number of target sample classification categories to obtain a plurality of target samples, and calculating respective times for the plurality of target samples to reach the third region of the interdigital transducers according to the respective moving speeds of the plurality of target samples, and generating respective delay enabling signals corresponding to the plurality of target samples according to the respective times.

5. The biological sample sorting method as recited in claim 4, wherein the operation of applying a second sinusoidal signal to the surface acoustic wave microfluidic chip according to the delay enable signal to control the target sample to move thus sorting out the target sample comprises:

when the target sample reaches the third region of the interdigital transducers, driving the signal generator to apply a continuous second sinusoidal signal to the third region of the interdigital transducers through the respective delay enable signal thus forming at least one node of the standing wave sound field in the channel, and adjusting a voltage of the applied second sinusoidal signal to control the target sample to move to the node position of the standing wave sound field thus sorting out the target sample.

6. The biological sample sorting method as recited in claim 1, wherein the Siamese neural network comprises two convolutional neural networks that share weights;

wherein inputs of the two convolutional neural networks are respectively a current frame and a sub-image containing the moving target in a previous frame;

wherein after being sampled and encoded by the convolutional neural networks, a result of the current frame is convoluted using a result of the sub-image containing the moving target thus obtaining a most similar region in the current frame image to the previous frame, so as to track the moving target.

\* \* \* \* \*